United States Patent [19]

Waterbury

[11] 4,454,151
[45] Jun. 12, 1984

[54] USE OF PYRROLO PYRROLES IN TREATMENT OF OPHTHALMIC DISEASES

[75] Inventor: L. David Waterbury, San Mateo, Calif.

[73] Assignee: Syntex (U.S.A.) Inc., Palo Alto, Calif.

[21] Appl. No.: 360,754

[22] Filed: Mar. 22, 1982

[51] Int. Cl.³ .............................................. A61K 31/40
[52] U.S. Cl. .................................................... 424/274
[58] Field of Search ......................................... 424/274

[56] References Cited

U.S. PATENT DOCUMENTS

| | | | |
|---|---|---|---|
| 4,087,539 | 5/1978 | Muchowski et al. | 424/274 |
| 4,089,969 | 5/1978 | Muchowski et al. | 424/274 |
| 4,097,579 | 6/1978 | Muchowski et al. | 424/274 |
| 4,140,698 | 2/1979 | Van Horn et al. | 424/274 |
| 4,232,038 | 11/1980 | Kluge et al. | 424/274 |
| 4,344,943 | 8/1982 | Muchowski et al. | 424/274 |

*Primary Examiner*—Douglas W. Robinson
*Attorney, Agent, or Firm*—Hana Dolezalova; Tom M. Moran; Alan M. Krubiner

[57] ABSTRACT

Certain known pyrrolo pyrroles have been found to be useful in the topical treatment of various ophthalmic diseases in mammals; especially those originating from or associated with inflammation such as, for example, cystoid macular edema, glaucoma, conjunctivitis, uveitis, diabetic retinopathy and eye surgery or trauma.

18 Claims, No Drawings

USE OF PYRROLO PYRROLES IN TREATMENT OF OPHTHALMIC DISEASES

BACKGROUND OF THE INVENTION

1. Field of the Invention

This invention relates to a method for the treatment of ophthalmic diseases originating from or associated with inflammation.

2. Related Disclosure

Many ophthalmic diseases are ocular disorders which are either caused or associated with painful inflammatory complications. Such complications very often lead to an impairment of the eyesight or blindness. Among those considered most dangerous belong glaucoma, cystoid macular edema, uveitis, diabetic retinopathy, conjunctivitis and postoperational or traumatic eye inflammation. When already developed all these ophthalmic diseases may be in acute, subacute or chronic form. The causes of ophthalmic inflammatory disorders may vary from bacterial, viral, fungal, parasitic, toxic, chemical, mechanical, irritative to allergic.

Glaucoma is a group of ocular diseases with the common features of abnormally elevated intraocular pressure which slowly causes progressive loss of peripheral visual fields and then untreated, it causes a loss of central vision and ultimate blindness. The causes of the development of glaucoma are unknown. Glaucoma is usually treated topically by agents which contract the eye pupil such as pilocarpine or carbachol, systemically by osmotic agents or carbonic anhydrase inhibitors, or radically by surgery. *The Merck Manual,* 13th Ed., 1702, (1977).

Cystoid macular edema is a retinal edema which may result from cataract removal. A newly proposed theory of the cause of a cystoid muscular edema is a release of prostaglandins or other inflammatory mediators derived from a disrupted blood-aqueous barrier into the aqueous. This theory is supported by findings that it is possible to subdue cystoid macular edema by the pre- and/or post-operative application of topical indomethacin, known suppressant of elevated levels of prostaglandins. *Albrecht v. Graefes Arch. Klin. Exp. Ophthal.,* 209:83-88, (1978).

Uveitis is an inflammation of the uveal tract encompassing inflammation of the iris, ciliary body and choroid. Uveitis may also develop following trauma where the ciliary body was injured. Predominant objective of the treatment of uveitis is suppression of damaging inflammatory activity. Dexamethazone drops, short-term systemic corticosteroid treatment or photocoagulation of the lesions are most commonly used for the treatment of uveitis. *The Merck Manual,* 13th Ed., 1697, (1977).

Diabetic retinopathy is microcirculatory complication associated with progressive form of the diabetes mellitus. It is characterized by proliferative neovascularization in the posterior pole of the eye often extending into vitreous cavity with subsequent vitreous hemorrhages, fibrous formation, and secondary retinal detachment and thickening of the capillary basement membrane. Treatments used to relieve severe symptoms of diabetic retinopathy include the strict control of blood pressure or laser photocoagulation of proliferating neovascular tufts to reduce the degree of retinal edema and the frequency and severity of hemorrhagic episode. *The Merck Manual,* 13th Ed., page 1700, (1977). In the pending application Ser. No. 162,355 applicants Ringold and Waterbury propose the systemic use of analgesics and non-hormonal anti-inflammatories in treatment of microvascular diseases.

Conjunctivitis is an inflammation of the conjunctiva and a mucous membrane characterized by a cellular infiltration and exudation. Conjunctivitis may be either acute, where the conjunctival inflammation is caused by viruses, allergy or bacteria; or chronic, where the inflammation of the conjunctiva is characterized by exacerbations and remissions that occur over the period of months or years. The causes for chronic conjunctivitis are similar to those of acute conjunctivitis. The treatment of both acute and chronic conjunctivitis include the topical administration of sulfonamide drops, antibiotic ointments, or systemic antibiotic therapy. The most important prevention of chronic conjunctivitis is elimination of all irritating factors. In the case of allergic conjunctivitis, topical corticosteroid therapy is also indicated. *Merck Manual* 13th Ed., page 1687 (1977).

Other inflammatory complications of the eye are those developing after the direct injury to the dye or those caused by trauma during the eye surgery. Injuries to the eye may be caused by foreign bodies, lacerations, contusions, burns, by chemicals, or others. The treatment of eye injuries and post-traumatic inflammations consists of anesthesia, precise diagnosis of the injury or trauma and post-traumatic or pre- or post-operative prevention of development of inflammation. *The Merck Manual,* 13th Ed., page 1680 (1977).

Compounds which are subject of this invention and those having similar structures to these compounds are known and have been described in U.S. Pat. Nos. 4,089,969; 4,232,038; 4,087,539 and 4,097,579. They are generally useful as a systemic anti-inflammatory, systemic analgesic and systemic antipyretic agents and smooth muscle relaxants. Their proposed uses as anti-inflammatories, antipyretics, analgesics or as a smooth muscle relaxants are in the form of tablets, capsules, suppositories, oral suspensions for systemic pediatric use or as a powdered top dressings for veterinary use. These compounds were not previously administered topically, i.e., directly to the eye, to prevent or treat ophthalmic diseases probably because their non-irritating properties are unexpected and surprising.

SUMMARY OF THE INVENTION

This invention is a method for prevention or treating ophthalmic diseases in mammals, which method comprises administering directly to the eye of a mammal in need thereof a pharmaceutically effective amount of a compound of the formula

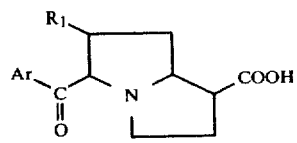

and the pharmaceutically non-toxic esters and salts thereof wherein Ar is

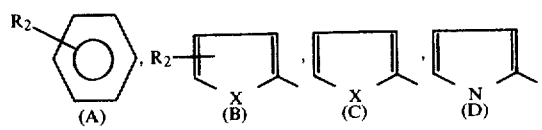

R₁ represents hydrogen; lower alkyl group having from one to four carbon atoms; chloro or bromo;

R₂ represents hydrogen, a lower alkyl group having from one to four carbon atoms, a lower alkoxy group having from one to four carbon atoms, chloro, bromo, fluoro; or R₄S(O)n wherein R₄ is lower alkyl and n is the integer 0, 1 or 2;

X represents oxygen or sulphur; and

The compounds which are particularly valuable in this regard are 5-benzoyl-1,2-dihydro-3H-pyrrolo(1,2-a)pyrrole-1-carboxylic acid;

5-(p-methylthio)benzoyl-1,2-dihydro-3H-pyrrolo(1,2-a)pyrrole-1-carboxylic acid; and 5-(p-methoxy)benzoyl-1,2-dihydro-3H-pyrrolo[1,2-a)pyrrole-1-carboxylic acid and the individual (l-) and (d-)acid isomers and pharmaceutically acceptable non-toxic alkyl esters and salts.

The invention also relates to a composition and preparation of the pharmaceutical ophthalmic solution for the treatment and prevention of ophthalmic diseases.

DETAILED DESCRIPTION OF THE INVENTION

Definitions

As used herein the "pharmaceutically acceptable non-toxic salt" derivatives of the compounds of formulas (A), (B), (C), (D), are those compounds wherein H of the COOH moiety is replaced by a positive ion such as for example sodium or is combined with a suitable amine. These salt derivatives are prepared as discussed hereinafter by reacting the acid of formula (A), (B), (C) or (D) with a suitable base.

The pharmaceutically acceptable non-toxic esters of formula (A), (B), (C) or (D) are those compounds wherein the OH of the COOH moiety is replaced by an alkoxy of 1 to 12 carbon atoms or an esterified glycerol. These are prepared as discussed hereafter by reacting an appropriate alcohol with the acid of formula (A), (B), (C) or (D).

The term "alkyl" refers to and includes branched and straight chain hydrocarbons containing the number of carbons indicated. Typical alkyl groups include methyl, ethyl, propyl, isopropyl, butyl, tertiary butyl, neopentyl, isopentyl, hexyl, octyl, nonyl, isodecyl, 6-methyldecyl.

The term "lower alkyl" means a branched or unbranched saturated hydrocarbon of 1-4 carbons, such as, for example, methyl, ethyl, n-propyl, i-butyl and the like.

The term "alkoxy" refers to a straight or branched chain alkyl ether groups wherein "alkyl" is as defined above. This includes radicals such as methoxy, ethoxy, 2-propoxy, butoxy, 3-pentoxy and the like.

"Lower alkoxy" means the group —OR wherein R is lower alkyl as herein defined.

"Halo" as used herein means a halogen ion chosen from those of fluoro, iodo, bromo, or chloro.

"Aroyl" as used herein refers to the radical R—CO— wherein R is five or six carbon aromatic group. Exemplary compounds of aroyl are benzoyl, 2-furoyl, 2-thenoyl, 3-furoyl or 3-thenoyl and the like.

In naming the compounds of this invention IUPAC nomenclature is used. The substituents attached to the aromatic ring are indicated by number of the carbon atom on the aromatic ring to which said substituent is attached according to the following scheme illustrations:

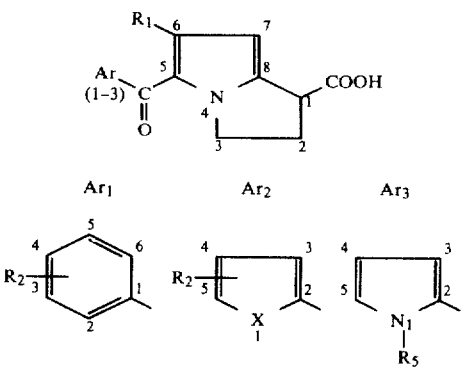

The R₂ substituent on the phenyl ring is at the ortho, meta or para positions, while the R₂ substituent on the furan or thiophene ring is at the 3, 4 or 5 position.

Preferred Embodiments

The broadest aspect of this invention is given in the "Summary of the Invention" in this specification. A preferred subgroup of compounds is represented by Formula (A), particularly those wherein R₁ is H or methyl and R₂ is H or methyl, methoxy, methylthio, or chloro at the para position.

Most preferred and exemplary compounds useful in the method of the present invention include, but are not limited to, 5-benzoyl-1,2-dihydro-3H-pyrrolo(1,2-a)-pyrrole-1-carboxylic acid, 5-(para-methylthio)benzoyl-1,2-dihydro-3H-pyrrolo(1,2-a)-pyrrole-1-carboxylic acid, 5-(para-methoxy)-benzoyl-1,2-dihydro-3H-pyrrolo(1,2-a)-pyrrole-1-carboxylic acid and individual (l-) and (d-) acid isomers thereof and the pharmaceutically acceptable nontoxic alkyl esters and salts.

Preparation Procedures

Detailed description of the preparation of 5-aroyl-1,2-dihydro-3H-pyrrolo[1,2-a]pyrrole-1-carboxylic acid compounds of Formula (A) and their pharmaceutically acceptable non-toxic esters and salts thereof is hereby incorporated by reference to the U.S. Pat. No. 4,089,969 to Muchowski et al, issued on May 16, 1978.

Detailed description of the preparation of 5-aroyl-6-chloro or 6-bromo-1,2-dihydro-3H-pyrrolo(1,2-a)pyrrole-1-carboxylic acid compounds of Formula (B) and the pharmaceutically acceptable non-toxic esters and salts thereof is hereby incorporated by reference to the patent application 06/157,719, to Muchowski, allowed on Apr. 22, 1981, not issued as yet.

Detailed description of the preparation of 5-substituted-1,2-dihydro-3H-pyrrolo(1,2-a)pyrrole-1-carboxylic acid of Formulas (B) and (C) and the pharmaceutically acceptable non-toxic esters and salts thereof is hereby incorporated by reference to the U.S. Pat. No. 4,087,539 to Muchowski et al, issued in May 2, 1978.

Detailed description of the preparation of 5-(2-pyrroyl) and 5-(N-lower alkyl-2-pyrroyl)-1,2-dihydro-3H-pyrrolo[1,2-a]pyrrole-1-carboxylic acid compounds of Formula (D) and the pharmaceutically acceptable nontoxic esters and salts thereof is hereby incorporated by The compound of Formula (III) is then converted to the corresponding 1-(2-methanesulfonyloxy)ethylpyrrol-2-yl-acetonitrile by esterification with methanesulfonyl chloride in the presence of a tertiary amine, i.e., triethylamine, pyridine and the like. Optionally, in the presence of a solvent such as dichloromethane, at a temperature from about $-10°$ C. to about room temperature, for about 10 minutes to about 2 hours esterification produces the corresponding mesyl ester. The mesyl ester represented by Formula (IV) is converted to the corresponding 1-cyano-1,2-dihydro-3H-pyrrolo-[1,2-a]pyrrole of Formula (V). By reaction with sodium iodide in acetonitrile solution, at reflux temperature for from about 1 to about 10 hours. The preparation of the compound of Formula (V) is discussed in U.S. Pat. No. 4,100,698 to Van Horn et al and that patent is incorporated herein by reference.

Nitrile of Formula (V) can be converted into the acid represented by Formula (VI) by reacting with aqueous sodium or potassium hydroxide in ethylene glycol at elevated temperatures of up to 120° C. for a time sufficient for the reaction to take place, generally less than about 5 hours. Extracting the reaction mixture with a suitable organic solvent, bringing the aqueous phase to an acid pH by using concentrated hydrochloric acid and extracting from water, results in the acid represented by Formula (VI). The acid, in turn, is converted to the ester of Formula (VII) by reaction with a lower aliphatic alcohol in the presence of an acid such as hydrochloric acid.

The carboxylic acid group at the C-1 position in compound (VI) is selectively esterified by treatment with a lower aliphatic alcohol, e.g., methanol, ethanol, isopropanol, n-butanol and the like in the presence of hydrogen chloride, to produce the corresponding alkyl 1,2-dihydro-3H-pyrrolo[1,2-a]pyrrole-1-carboxylic acid of Formula (VII). The reaction is conducted at a temperature of from about 0° to about 50° C., for about 1 to about 4 hours.

A compound of Formula (VII) is then converted to the alkylthiobenzoyl compound of Formulas (VIII) and (A) by a condensation of a compound (VII) with either an acid chloride of the formula

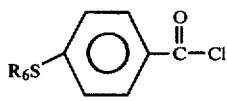

or a reagent prepared from an amide of the formula

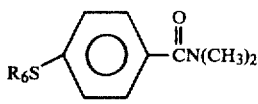

and phosphorus oxychloride wherein $R_6$ has the above-indicated meaning, affords the corresponding alkyl 5-benzoyl-1,2-dihydro-3H-pyrrolo[1,2-a]pyrrole-1-carboxylic acid (VIII). This is done following process conditions set forth in U.S. Pat. No. 4,089,969.

In the preferred embodiment of this process, this condensation is carried out by adding a solution of compound of Formula (VII) in a suitable solvent to a previously refluxed mixture of 1.1 to 5 molar equivalents of both the desired amide and phosphorus oxychloride in the same solvent, refluxing the reaction mixture thus obtained for from about 6 to about 72 hours under an argon atmosphere and thereafter adding thereto from about 3 to about 10 molar equivalents of sodium acetate, followed by an additional reflux period for from about 4 to about 6 hours.

Alternatively, the intermediate nitrile of Formula (V) can be converted into the nitrile of Formula (IX) in Reaction Scheme using reaction conditions discussed hereinbefore in the conversion of the compound of Formulas (VII) to (VIII). The compound of Formula (IX), in turn, is converted to a compound (A) of the invention by converting the nitrile moiety to an acid as discussed hereinbefore.

The compounds of Formula (A) can be resolved, according to methods known in the art, to obtain the corresponding individual isomers thereof.

The (l)-acid isomers and (d)-acid isomers of the compounds of Formula (A) can be obtained by applying the known technique of high pressure liquid chromatography (HPLC) to the α-phenethyl diastereoisomeric esters of the compounds of Formula (A), followed by acid cleavage. Thus, for example, the compounds of Formula (A) wherein $R_1$ and $R_6$ are both hydrogen can be subjected to further treatment in accordance with the following flow diagram:

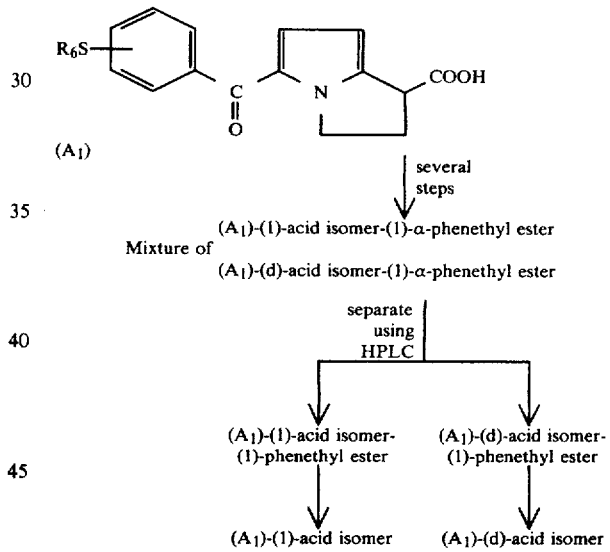

The free acids of Formula (A), (B), (C) and (D) can be converted into other alkyl esters having from 1 to 12 carbon atoms by conventional methods, e.g., by treatment with (a) the alcohol corresponding to the desired ester in the presence of a strong mineral acid, (b) an ethereal diazoalkane or (c) the desired alkyl iodide in the presence of lithium carbonate.

The salt derivatives of the compounds of Formula (A), (B), (C) and (D) are prepared by treating these free acids with an appropriate amount of a pharmaceutically acceptable base. Representative pharmaceutically acceptable bases are sodium hydroxide, potassium hydroxide, lithium hydroxide, ammonium hydroxide, calcium hydroxide, magnesium hydroxide, ferrous hydroxide, zinc hydroxide, copper hydroxide, manganous hydroxide, aluminum hydroxide, ferric hydroxide, manganic hydroxide, isopropylamine, trimethylamine, diethylamine, triethylamine, tripropylamine, ethanolamine, 2-dimethylaminoethanol, 2-diethylaminoereference to the U.S. Pat. No. 4,097,579 to Muchowski et al, issued in June 27, 1978.

Detailed description of the preparation of 5-alkylsulfinylbenzoyl- and 5-alkylsulfonylbenzoyl-2-dihydro-3H-pyrrolo[1,2-a]pyrrole-1-carboxylic acid compounds of Formula (A) and their pharmaceutically acceptable non-toxic esters and salts is hereby incorporated by reference to the U.S. Pat. No. 4,232,038 to Kluge et al, issued on Nov. 4, 1980.

5-alkylthiobenzoyl-1,2-dihydro-3H-pyrrolo[1,2-a]pyrrole-1-carboxylic acid compounds of Formula (A) are prepared by a process illustrated by the following reaction sequence.

basic alcohol mixture such as sodium hydroxide and methanol at room temperature to give solely the desired product represented by formula (I).

This in turn is reacted at slightly elevated temperatures, e.g. 20°-60° C., with a solution of dimethylamine hydrochloride in aqueous formaldehyde to give 1-(2-hydroxyethyl)-2-dimethylaminomethylpyrrole (II). After extraction with a suitable organic solvent such as dichloromethane and subsequent purification by evaporation and distillation, the compound represented by Formula (II) is then dissolved in acetone and is maintained in an inert atmosphere using nitrogen or argon and a slight molar excess of dimethylsulfate is added to

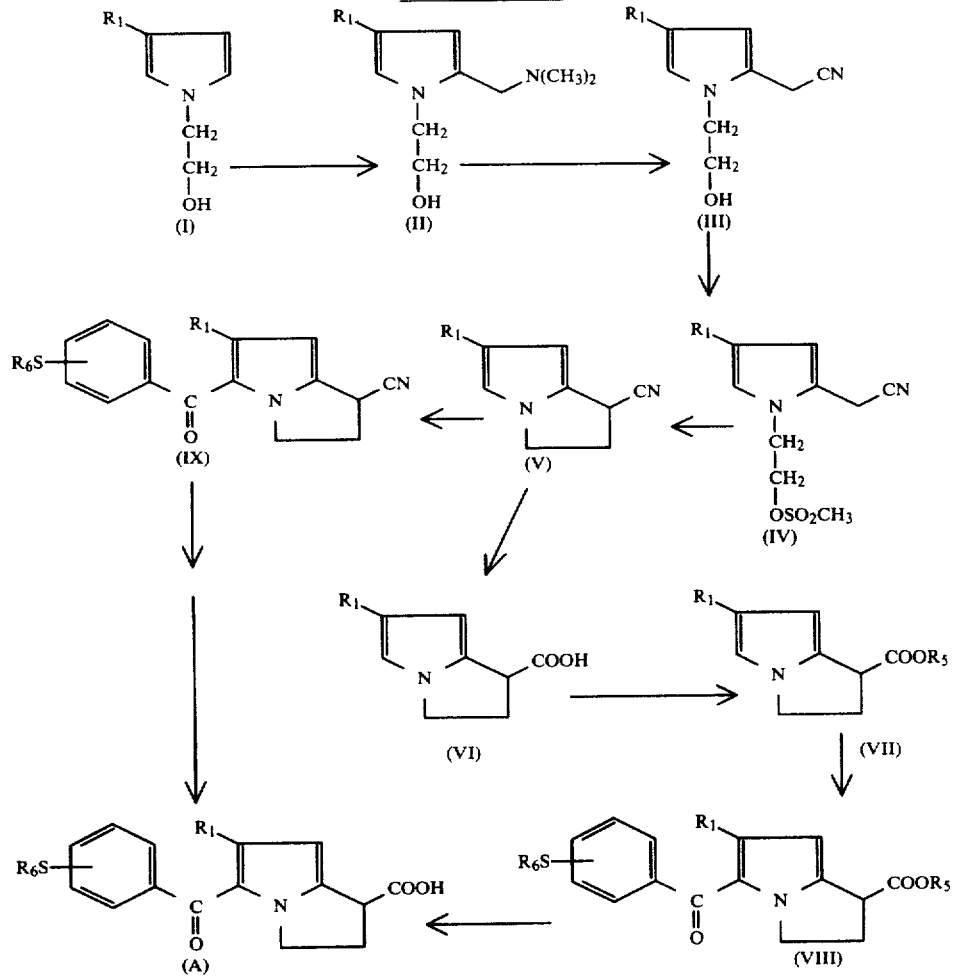

Reaction Sequence $R_1$ represents hydrogen; lower alkyl group having from one to four carbon atoms; chloro or bromo;

$R_5$ represents methyl, ethyl, isopropyl or n-butyl depending on whether methanol, ethanol, isopropanol or n-butanol are used for esterification;

$R_6$ represents alkyl;

The starting compound 2-aminoethanol acetate (not shown) is prepared by reacting 2-aminoethanol with glacial acetic acid at a temperature of between 5° and 50° C. This compound is then reacted with dimethoxytetrahydrofuran at reflux temperature for a period of time sufficient to give the desired pyrrole and the corresponding acetate. The reaction takes generally less than about 5 hours. After extracting the product from the reaction mixture, the mixture is hydrolyzed using a the cooled reaction mixture at such a rate that the temperature does not exceed about 5° C. When addition of the dimethylsulfate is completed, the solution is stirred at room temperature and a solution of sodium cyanide in water is added. The resulting reaction mixture is heated to reflux temperature, i.e. generally about 90°-100° C. and the distillate is collected. The reaction mixture is heated at a gentle reflux for a suitable period of time, generally less than 2 hours, preferably about ½ hour and water is added to the mixture. After extracting, drying and purification by column chromatography, a nitrile represented by Formula (III) is obtained, namely 1-(2-hydroxyethyl)pyrrol-2-yl-acetonitrile.

thanol, tromethamine, lysine, arginine, histidine, caffeine, procaine, hydrabamine, choline, betaine, ethylenediamine, glucosamine, methylglucamine, theobromine, purine, piperazine, piperidine, N-ethyl-piperidine, polyamine resins and the like. The reaction is conducted in water, alone or in combination with an inert, water-miscible organic solvent, at a temperature of from about 0° to about 100° C., preferably at room temperature. Typical inert, water-miscible organic solvents include methanol, ethanol, isopropanol, butanol, acetone, dioxane or tetrahydrofuran. The molar ratio of compounds of Formula (A), (B), (C) and (D) to base used are chosen to provide the ratio desired for any particular salt. For preparing, for example, the calcium salts or magnesium salts of the compounds of Formula (A), (B), (C) and (D) the free acid starting material can be treated with at least one-half molar equivalent of pharmaceutically acceptable base to yield a neutral salt. When the aluminum salts of the compounds of Formula (A), (B), (C) and (D) are prepared, at least one-third molar equivalent of the pharmaceutically acceptable base are employed if a neutral salt product is desired.

In the preferred procedure, the calcium salts and magnesium salts of the compounds of Formula (A), (B), (C) and (D) can be prepared by treating the corresponding sodium or potassium salts thereof with at least one-half molar equivalent of calcium chloride or magnesium chloride, respectively, in an aqueous solution, alone or in combination with an inert water-miscible organic solvent, at a temperature of from about 20° to about 100° C. Preferably, the aluminum salts of the compounds hereof, can be prepared by treating the corresponding free acids with at least one-third molar equivalent of an aluminum alkoxide, such as aluminum triethoxide, aluminum tripropoxide and the like, in a hydrocarbon solvent, such as benzene, xylene, cyclohexane and the like, at a temperature of from about 20° to about 115° C. Similar procedures can be used to prepare salts of inorganic bases which are not sufficiently soluble for easy reaction.

The salt derivatives of the compounds of formula (A), (B), (C) and (D) can be reconverted to their respective free acids by acidifying said salts with an acid, preferably an inorganic acid, e.g., hyrochloric acid, sulfuric acid, and the like, at temperature of from about 0° C. to about 50° C., preferably at room temperature.

The pharmaceutically acceptable non-toxic esters of formula (A), (B), (C) and (D) are prepared by esterifying the corresponding free acids with an alcohol reagent corresponding to the desired ester, e.g., an alkanol having up to 12 carbon atoms or with glycerol which is already esterified at two hydroxyls to other suitable acids. This reaction is conducted in the presence of a strong acid, such as boron trifluoride, hydrogen chloride, sulfuric acid, p-toluenesulfonic acid, and the like. If the alcohol reagent used in the esterification is a liquid at the reaction temperature, the alcohol reagent can be the reaction solvent. Optionally, the reaction can be carried out in an inert organic solvent in which the free acids and the alcohol reagent are soluble, such as a hydrocarbon solvent, e.g., hexane, isooctane, decane, cyclohexane, benzene, toluene, xylene, a halogenated hydrocarbon solvent, e.g., methylene chloride, chloroform, dichloroethane; or an ether solvent, e.g., diethyl ether, dibutyl ether dioxane, tetrahydrofuran, and the like. In the case where the alcohol reagent is a solid, the reaction preferably is conducted in a non-aqueous liquid inert organic solvent. The reaction is conducted at from about 0° C. to the reflux temperature of the reaction mixture, preferably using hydrogen chloride at a temperature of from 15° C. to about 35° C.

The product is isolated by conventional means such as diluting the reaction mixture with water, extracting the resulting aqueous mixture with a water-immiscible inert organic solvent, such as diethyl ether, benzene, methylene chloride, and the like, combining the extracts, washing the extracts with water to neutrality and then evaporating under reduced pressure.

Typical esters are those ester derivatives prepared from methyl alcohol, ethyl alcohol, propyl alcohol, isopropyl alcohol, butyl alcohol, 2-butyl alcohol, 2-pentyl alcohol, isopentyl alcohol, 2-hexyl alcohol, and the like.

Alternatively, the alkyl esters can be prepared by transesterification, according to methods known in the art. It is preferred in preparing the esters via transesterification to go from a lower ester to a higher ester, e.g., from the methyl ester, for example, to the isoamyl ester, for example. However, by using a substantial excess of a lower alcohol, a higher ester can be transesterified to a lower ester; thus, for example, by using a substantial excess of ethanol, the hexyl ester is converted by the transesterification to the ethyl ester.

It is to be understood that isolation of the compounds described herein can be effected, if desired, by any suitable separation or purification procedure, such as for example, extraction, filtration, evaporation, distillation, crystallization, thin-layer chromatography or column chromatography, high pressure liquid chromotography (HPLC) or a combination of these procedures.

The novel compounds of Formula (A), (B), (C) and (D) depicted above exist as pairs of optical isomers (or enantiomorphs), i.e., a (dl) mixture. However, each optical isomer as well as the (dl) mixtures thereof are included within the present invention.

While the (d)-acid isomers are not used as a medicinal of agents per se, they can, if desired, be converted to their pharmaceutically acceptable, nontoxic esters and salts thereof according to the methods described for the conversion of the (1-) acid isomers to their pharmaceutically acceptable, nontoxic esters and salts thereof.

Utility and Administration

This invention is directed to method useful for relieving, inhibiting or preventing ophthalmic diseases in mammals. These diseases may be, among others, glaucoma, cystoid macular edema, uveitis, diabetic retinopathy, conjunctivitis or any trauma caused by eye surgery or eye injury and which are either caused by, associated with, or accompanied by inflammatory processes.

The method of this invention is both curative and preventative. Where applied, for example, pre-surgically or immediately post-traumatically, i.e. before inflammation develops, it prevents development of inflammation. When applied directly to the eye suffering from any of the named ophthalmic diseases, it supresses already developed inflammatory processes. Thus, for example, a topical application of appropriate ophthalmic solution with active ingredient to the eye suffering from glaucoma, will not only stop further increase in intraoccular pressure but it will also descrease the pressure to its normal level.

The human eye is an excellent subject for the topical administration of drugs. The basis of this can be found in the anatomical arrangement of the surface tissues and in the permeability of the cornea. The protective operation of the eyelids and lacrimal system is such that there is rapid removal of material instilled into the eye, unless the material is chemically and physiologically compatible with surface tissues.

The optical apparatus consists, in sequence, of the cornea, the pupil, and the crystalline lens, with layers of clear fluid or gel-like material interposed between the solid structures. The pupil, a round centric hole in a contractile membranous partition (called the iris), acts as the variable aperture of the system. The crystalline lens is a refractive element with variable power controlled and supported by a muscle incorporated in the ciliary body. The chloroid is the metabolic support for the retina.

The optical function of the eye calls for the stability of its dimensions which is provided partly by the fibrous outer coat; more effective as a stabilizing factor is the intraocular pressure which is in excess of the pressure prevailing in the surrounding tissues. This intraocular pressure is the result of a steady production of specific fluid, the aqueous humor, which originates from the ciliary processes and leaves the eye by an intricate system of outflow channels. The resistance encountered during this passage and the rate of aqueous production are the principal factors determining the level of the intraocular pressure. In addition to this hydromechanical function, the aqueous humor acts as a carrier of nutrients, substrates, and metabolites for the avascular tissues of the eye.

The conjunctival membrane covers the outer surface of the white portion of the eye and the inner aspect of the eyelids. In most places it is loosely attached and thereby permits free movement of the eyeball. This makes possible subconjunctival injections. Except for the cornea, the conjunctiva is the most exposed portion of the eye; thus, the most susceptible to infection.

The conjunctival and corneal surfaces are covered and lubricated by a film of fluid secreted by the conjunctival and the lacrimal glands. The secretion of the lacrimal gland, the tears, is delivered through a number of fine ducts into the conjunctival fornix. The secretion is a clear, watery fluid containing 0.7% protein and the enzyme lysozyme. Small accessory lacrimal glands are situated in the conjunctival fornices. Their secretion suffices for lubrication and cleansing under ordinary conditions and for maintaining a thin fluid film covering the cornea and conjunctiva (the precorneal film).

The cornea is transparent anterior portion of the outer coat of the eye. The normal cornea possesses no blood vessels except at the corneoscleral junction. The cornea, therefore, must derive its nutrition by diffusion and must have certain permeability characteristics; it also receives nourishment from the fluid circulating through the chambers of the eye and also from the air.

Cloudiness of the cornea may be due to any one of several factors including excess pressure in the eyeball (as in glaucoma); scar tissue (due to injury or infection); or deficiency of oxygen or excess hydration (as may occur during the wearing of improperly fitted contact lenses). A wound of the cornea usually heals as an opaque patch which may result in a permanent disability unless it is located in the periphery of the cornea.

The corneal epithelium provides an efficient barrier against bacterial invasion. Unless its continuity has been broken by an abrasion (a traumatic opening or defect in the epithelium) pathogenic bacteria, as a rule, cannot gain a foothold. Trauma, therefore, plays an important part in most of the infectious diseases of the cornea which occur exogenously. Any foreign body which either scratches the cornea or lodges and becomes imbedded in the cornea is of serious moment because of the role it may play in permitting pyogenic bacteria to gain a foothold.

The therapeutic effect of many topically administered (instilled) drugs is contingent upon their absorption from the cul-de-sac into the eye. Drugs which are administered by instillation and which must penetrate into the eye enter primarily through the cornea. This is a much more effective route of administering the drug into the eye than through the conjunctiva and underlying sclera.

The conjunctiva contains many blood vessels and lymphatic vessels. The blood vessels usually dilate when irriation is set up by a foreign body, a microbial infection, or by chemical means. Of the drug molecules which penetrate into the conjunctiva a large proportion enters the blood stream where they may cause undesirable systemic reactions. Below the conjunctiva lies the sclera, which water-soluble drugs penetrate with ease and which lipoid-soluble drugs penetrate with difficulty.

In the non-inflamed eye, the blood-aqueous barrier, constituted of the blood vessel wall and various thicknesses of the ocular tissues, prevents certain drugs from reaching the anterior segment in therapeutic concentrations if administered systemically.

In the inflamed eye permeability of the blood-aqueous barrier is increased, allowing few drugs adminsistered systemically in therapeutic quantities to reach the anterior chamber of an inflamed eye, but many more drugs will have such effect only if administered systemically in quantities that would cause harm in other parts of the body. In general, in the treatment of the anterior segment of the eye, such systemic administration does not accomplish as much as topical administration.

The compounds of Formulas (A), (B), (C) and (D) and their pharmaceutically acceptable non-toxic alkyl esters and salts (described hereinabove) have been found, in animal experiments, to be non-irritating, hence physiologically compatible, and yet to have a profound antiinflammatory effect when applied directly to the eye. Thus, these compounds are highly potent in penetrating occular tissue but, surprisingly, upon their topical application, they show no irritation of the occular tissue. Compounds of this invention show considerable biological activities effecting especially neovascularization experimentally induced by silver nitrate, uveitis experimentally induced by endotoxin, or glaucoma-like increase in intraoccular pressure induced by arachidonic acid. Accordingly, these compounds, when applied topically, offer a method for treating occular disorders caused or associated with inflammatory processes of the mammalian eye without exposing the mammal to the danger of secondary symptoms caused by large dosages required for systemic treatment.

In the practice, the compounds of the invention or their pharmaceutically acceptable non-toxic alkyl esters and salts are administered topically, i.e., directly to the eye of a subject suffering from inflammatory complications of the eye. Administration is in the form of ophthalmic preparation applied directly to the eye.

Ophthalmic preparations are sterile products for either topical application to the eyelids or instillation into the space (cul-de-sac) between the eyeball and the eyelids. Presently available ophthalmic preparations include solutions, suspensions, and ointments. Presently available topical treatment of eye diseases include topically applied ophthalmic drops, solutions, suspensions or ointment or their subconjunctival injection.

Most ophthalmic solutions are so formulated as to mix readily with the lacrimal fluids and spread over the surfaces of the cornea and conjunctiva. With the usual technique of installation the major portion of the drug is deposited in the lower fornix. Capillarity, diffusional forces, and the blinking reflex are the forces that bring about the incorporation of the drug in the precorneal film from which it penetrates into and through the cornea.

Studies have indicated that a substance will pass through the cornea most easily if it has a biphasic solubility; that is, if it is soluble both in fat and in water.

The cornea can be penetrated by ions to a small, but measurable, degree. Under comparable conditions, the permeabilities are similar for all ions of small molecular weight, which suggests that the passage is through the extracellular spaces. The diameter of the largest particles which can pass across the cellular layers seem to be in the range of 10–25 Å. Increase in the permeability of the cellular layers can be produced by experimental techniques which involve slight manipulations such as touching the cornea, or instilling solutions differing in tonicity from that of the body fluids, or even stirring the solution in contact with the corneal surface.

The composition of this invention comprises, as active ingredient, a compound of formula (A), (B), (C) or (D) or an ester or salt thereof as described hereinabove, in admixture with an ophthalmologically acceptable excipient. An excipient is ophthalinologically acceptable if it is non-irritating to the eye and if its active ingredient penetrates the blood-aqueous barrier and/or difuse to or through the various ocular substructures to the site where it is pharmacologically active. The composition may be and may be aqueous or non-aqueous, on the form of a solution, suspension, gel, ointment, slow release polymer, or other. Amount of active ingredient will vary with the particular formulation and disease state but generally will be betweeen 0.001–10 percent of active ingredient per individual application dose.

Pharmaceutical ophthalmic compositions are typically sterilized aqueous solutions (i.e. eyedrops) containing 0.001% to 10% wt/vol.; most preferably 0.005% to 1% of the active ingredient, along with suitable buffer, stabilizer, and preservative. The total concentration of solutes should be such that, if possible, the resulting solution is isotonic with the lacrimal fluid (though this is not absolutely necessary) and has an equivalent pH in the range of pH 6–8. Typical preservatives/sterilants are phenylmercuric acetate, thimerosal, chlorobutanol, and benzalkonium chloride. Typical buffer systems and salts are based on, for example, citrate, borate or phosphate; suitable stabilizers include glycerin and polysorbate 80. The aqueous solutions are formulated simply by solutes in a suitable quantity of water, adjusting the pH to about 6.8–8.0, making a final volume adjustment with additional water, and sterilizing the preparation using method known to those in the art.

The dosage level of the resulting composition will, of course, depend on the concentration of the drops, the condition of the subject and the individual magnitude of responses to treatment. However, typical dosage ranges might be about 2–10 drops of 0.1% solution of active ingredient per day.

Most ophthalmic solutions and suspensions contain an aqueous rather than an oily vehicle. Ophthalmic ointments usually contain a white petrolatam-mineral oil base, often including anhydrous lanolin, while some have a polyethylene-gelled mineral oil base.

Solutions are the most commonly used type of preparation for the local medication of eyes. They are easily instilled and rarely cause adverse reactions. The vehicle does not cause interference with vision and does not interfere with regeneration of the corneal epithelium.

Oily solutions such as for medicaments which are incompatible with water are infrequently used. The only official ophthalmic solution using oil is that of isoflurophate.

Suspensions have the advantage of more extended action and the disadvantage that it is difficult to avoid the presence of a few particles which are large enough to cause irritation.

Eye ointments are sterile preparations for application to the conjunctival sac or lid margin. They have advantages of more prolonged contact and effect, hardly any irritation on initial installation, slower movement into lacrimal ducts, greater storage stability, and less likelihood of contamination problems. Their disadvantages are that they produce a film over the eye and thereby blur vision; and they may interfere with the firm attachment of new corneal epithelial cells to their normal base. Ointments affect the outside and edges of the eyelids, the conjunctiva, the cornea, and the iris, depending on their ability to penetrate the outer covering of the eyeball. Topical drugs can affect the anterior chamber (between the cornea and the iris), the ciliary body (part of which holds the lens and adjusts its shape), and the lens.

Ophthalmic ointments comprising active ingredients can be used for the effect of a variety of medicaments on the outside and edges of the eyelids, the conjunctiva, the cornea, and the iris. Most ophthalmic ointments are prepared with a base of white or yellow petrolatum and mineral oil, often with added anhydrous lanolin. Whichever base is selected, it must be nonirritating to the eye, permit diffusion of the drug throughout the secretions bathing the eye, anbd retain the activity of the medicament for a reasonable period of time under proper storage conditions.

A suitable basis for eye ointments is given by the following formula:

| Liquid Paraffin | 100 g |
|---|---|
| Wool Fat | 100 g |
| Yellow Soft Paraffin | 800 g |

The wool fat, the yellow soft paraffin and the liquid paraffin are heated together, filtered whie hot through a course filter paper in a heated funnel, sterilized by heating for a sufficient time to ensure that the whole of the basis is maintained at a temperature of 150° for one hour, and allowed to cool, taking precautions to avoid contamination with micro-organisms, before incorporating the sterile medicament.

Eye ointments are prepared, by means of an aseptic technique, by either of the following methods:

Method A. If the medicament is readily soluble in water forming a stable solution, it is dissolved in the minimum quantity of water and the solution sterilized by autoclaving or by filtration and incorporated gradually in the melted sterile basis, the mixture being stirred continuously until it is cold. The eye ointment is then transferred to the final sterile containers, which are closed so as to exclude micro-organisms.

Method B. If the medicament is not readily soluble in water or if the aqueous solution is unstable, the medicament is finely powdered, thoroughly mixed with a small quantity of the melted sterile basis, and then incorporated with the remainder of the sterile basis. The eye ointment is then transferred to the final sterile containers, which are closed so as to exclude microorganisms.

If the medicament is insoluble in both water and the basis, it is essential that it be reduced to an extremely fine powder before incorporating with the basis, in order to avoid irritation to the eye.

It is obligatory that ophthalmic ointments do not contain particulate matter that may be harmful to eye tissues. Hence, in preparing such ointments special precaution is taken to exclude or to minimize contamination with foreign particulate matter, e.g., metal particles fragmented from equipment used in preparing ointments, and also to reduce the particle size of the active ingredient(s) to impalpability. The official compendia provide tests designed to limit to a level considered to be unobjectionable the number and size of discrete particles that may occur in ophthalmic ointments. In these tests the extruded contents of tubes of ointment, previously melted in flat-bottom Petri dishes and then allowed to solidify, are scanned under a low-power microscope fitted with a micrometer eyepiece for (1) metal particles $50\mu$ or larger in any dimension and (2) other particles $50\mu$ or larger in any dimension. The limit for each kind of particle is 50 in a total of 10 tubes of ointment and 8 in not more than 1 of the 10 tubes.

Testing for sterility of products such as ophthalmic ointments has been greatly facilitated by use of sterile bacteria-retaining membranes (those having a nominal porosity of $0.45\mu$ are commonly used). For ointments soluble in isopropyl myristate (the solvent used in the official test for sterility) a sample of the ointment is dissolved in the sterile solvent and filtered through the sterile membrane which, after washing with sterile rinse medium, is subjected to the sterility test. For ointments insoluble in isopropyl myristate the sample is suspended in a suitable aqueous vehicle that may contain a dispersing agent.

For a long time the technology available for manufacture of ophthalmic ointments was not adequate to produce sterile products; indeed it was believed by some to be impossible to operate a tube-filling machine so as to maintain sterility even in a sterile room. In recent years technological advances have made is possible to manufacture sterile ophthalmic ointment units. Major improvement was achieved in the area of filtration technology. Membrane filters have improved and reliability of both sterile filtration procedures and sterility-testing methods. Use of laminar flow of HEPA-filtered air in appropriately designed rooms and hoods has been a major factor in the successful aseptic operation of the roller mill and of devices for filling tubes with ointment.

The official compendia direct that ophthalmic ointments be prepared from previously sterilized ingredients, under rigidly aseptic conditions. Petrolatum vehicles and many medicaments may be sterilized by heating in a hot-air oven at 150° C. for 2 hours; utensils required for compounding may be sterilized by autoclaving; empty tubes may be sterilized by storage for 24 hours in a 1:1000 solution of benzalkonium chloride in 70% isopropyl alcohol followed by removal of alcohol by evaporation. A sterile disposable syringe without a needle may be used to transfer the finished ointment, if it is semi-fluid, to the ointment tube, or sterile aluminum foil or powder paper may be used for the same purpose. Probability of microbial contamination is greatly reduced by carrying out selected steps of the procedure in a laminar-flow hood.

Compounds of this invention may also be administered by other nonsystemic modes. Ophthalmic packs may be used to give prolonged contact of the solution with the eye. A cotton pledget is saturated with an ophthalmologically suitable solution and this pledget is inserted into the superior or inferior fornix. Packs are commonly used to produce maximal mydriasis. In this case the cotton pledgets can be, for example, saturated with a solution of a compound of this invention. Medicated ophthalmic disks produce mitosis both more intense and prolonged than either solution. Use of disks may be preferable to use of solutions.

The compounds may also be administered by the way of iontophoresis. This procedure keeps the solution in contact with the cornea in an eyecup bearing an electrode. Diffusion of the drug is effected by difference of electrical potential.

Subconjunctival injections of compounds of the current invention may be used to introduce medications which, if instilled, either do not penetrate into the anterior segment or penetrate too slowly for the desired effect. The drug is injected underneath the conjunctiva and propably passes through the sclera and into the eye by simple diffusion. The most common use of subconjunctival injection is for the administration of antibiotics in infections of the anterior segment of the eye. Subconjunctival injections of mydriatrics and cycloplegics are also used to achieve maximal pupillary dilation or relaxation of the ciliary muscle. If the drug is injected underneath the conjunctiva and the underlying Tenon's capsule in the more posterior portion of the eye, effects on the ciliary body, choroid, and retina can be obtained.

Drugs may also be administered by retrobulbar injection whereby they enter the globe in essentialy the same manner as the medications given subconjunctivally. The orbit is not well vascularized and the possibility of significant via-blood stream effects of retrobulbar injections is very remote. In general, retrobulbar injections are given for the purpose of getting medications into the posterior segment of the globe and to affect the nerves and other structures in the retrobulbar space. *Remington's Pharmaceutical Sciences*, 15th Ed., 1489-1504, (1975).

The following examples are intended to illustrate, but not to limit, the scope of the invention.

EXAMPLE 1

Composition of Ophthalmic Solutions for Topical Administration to the Eye

| Ingredient | Composition at Concentration Indicated | | | | |
|---|---|---|---|---|---|
| | Vehicle | 0.02% | 0.1% | 0.25% | 0.5% |
| $NaH_2PO_4.H_2O$ 0.2 M | 8 ml | 8 ml | 8 ml | 8 ml | 8 ml |
| $Na_2HPO_4.H_2O$ 42 ml 0.2 M | 42 ml | 42 ml | 42 ml | 42 ml | |
| Active Ingredient | 0 | 0.02 g | 0.1 g | 0.25 g | 0.5 g |
| NaCl | 0.18 g | 0.178 g | 0.165 g | 0.142 g | 0.10 g |

-continued

| Ingredient | Composition at Concentration Indicated | | | | |
|---|---|---|---|---|---|
| | Vehicle | 0.02% | 0.1% | 0.25% | 0.5% |
| Benzalkonium Chloride 50% w/w | 0.02 g | 0.02 g | 0.02 g | 0.02 g | 0.02 g |
| Sterilized water q.s. | 100 ml | 100 ml | 100 ml | 100 ml | 100 ml |

The active ingredient in this example is 5-benzoyl-1,2-dihydro-3H-pyrrolo(1,2-a)pyrrole-1-carboxylic acid, but other compounds of this invention may be substituted therefor.

The active compound of this example, in its trishydroxymethylaminomethane salt, was dissolved in buffered isotonic solutions containing benzalkonium chloride as a preservative. Volume was made up to 100 ml and pH adjusted to 7.4. The resulting solution was filtered through 0.45 microns millipore filter and were dispensed for use in dropper bottles.

EXAMPLE 2

Eye Irritation Study

This example illustrates non-irritating properties of compounds of this invention when used as topical anti-inflammatories administered directly to the eye of an experimental animal.

To be effective topical anti-inflammatory agent, the compound must, first of all, itself prove to be non-irritating. To determine the effects of various compounds on eye irritation, the comparative irritability test among known anti-inflammatories was designed wherein the irritation of the eye following the topical application of tested compound was measured and compared to the irritation of the eye following the application of other anti-inflammatory compound. Each studied anti-inflammatory compound was tested individually on single animal by administering, at the same time, into one eye of the animal the ophthalmic solution with tested compound as an active ingredient and to the other eye vehicle ophthalmic solution only. An irritation caused by tested compounds, if any, was compared to non-irritating effect of vehicle ophthalmic solution applied to the other eye. Irritation was measured by number of blinks of each eye during the exact period of time. Tests were performed on rats, dogs and monkeys.

Protocol

Ophthalmic solutions with the 0.02%, 0.1% and 0.5% of 5-benzoyl-1,2-dihydro-3H-pyrrolo(1,2-a)pyrrole-1-carboxylic acid or Flurbiprofen as an active ingredient were prepared according to the procedure of Example 1. One drop of the tested ophthalmic solution with active ingredient was administered directly into the conjuctival sack of the rat's left eye. At the same time one drop of vehicle was administered to the conjunctival sack of the rat's right eye. Irritation of each eye was measured by counting the number of blinks for one minute after the application. The results were expressed as the mean number of blinks±standard error per eye. The mean number of blinks/minute were averaged for the vehicle treatment and compared to the drug treated eye. Each compound was tested similarly in mongrel dogs and rhesus monkeys.

While Flurbiprofen has caused a severe eye irritation (it, for example, doubled number of blinks following the application of 0,5% solution) in rats, dogs and monkeys, the compounds of this invention did not illicite any irritation of the eyes in any of the three species at any concentration which was used for testing (i.e., 0,002-0.5%) and their effect was comparable to the effect of the vehicle ophthalmic solution without any drug added.

EXAMPLE 3

Silver nitrate-induced neovascularization

This example illustrates topical anti-inflammatory effect of claimed compounds by testing their ability to inhibit neovascular growth induced by silver nitrate cauterization.

Corneal neovascularization is part of the normal inflammatory response to the keratitis—inflammation of the cornea. Corneal neovascularization follows corneal invasion by polymorphonuclear leukocytes. The most serious consequence of neovascularization is the loss of corneal transparency combined with a biochemical modification of the corneal tissue that changes it from an avascular tissue not participating in the body's tissue immunity to one requiring a direct blood supply that partakes of antigen-antibody reactions. Experimentally, neovascularization of the cornea may be induced by cauterization of the rat or rabbit cornea with silver nitrate. *Amer. J. Pathol.* 79: 537. 1975.

Protocol

Preliminary experiments have shown that rats elicited a more uniform response to a silver nitrate than rabbits. Four groups of rats (12/group) were used for this study. The center of the each rat's cornea was cauterized with silver nitrate applicator stick obtained from San Jose Surgical Supply. Treatment was started immediately after cauterization and comprised a topical administration of various concentrations of tested compounds of vehicle directly to the rat's eye.

Vehicle ophthalmic solution and ophthalmic solution with 0.1%, 0.25% or 0.5% of 5-benzoyl-1,2-dihydro-3H-pyrrolo(1,2-a)pyrrole-1-carboxylic acid as an active ingredient were prepared according to the procedure of Example 1. Immediately after cauterization, one drop of tested ophthalmic solution was applied to the right eye and one drop of the vehicle was applied to the left eye four times each day always administering solutions containing tested compound or vehicle to the same eye as previously. Treatment was continued for 5 days.

It has been found that cauterization caused a wide response and therefore the response to burning was graded to ensure that the mean response for each group was similar. The following scale was used to grade the response to burning.

| | |
|---|---|
| 0 | no burn visible |
| 1+ | cauterized area with no blister |
| 2+ | small blister |
| 3+ | moderate blister |
| 4+ | large blister |

Because the burns which do not cause a blisters do not induce neovascularization, prior to a treatment initiation, rats were examined for the presence or absence of blisters and the rats who did not develop blisters were excluded from the study. Thus, the only rats with burns degree of 2+ to 4+ were used.

The day after the last treatment, the degree of the neovascularization which developed around the cornea was quantitated by determining the distance which the new blood vessels progressed toward the burn site. The following scale was used to determine the degree of the neovascularization:

| | |
|---|---|
| 0 | blood vessels in cornea |
| 1.5+ | blood vessels ¼ distance to burn |
| 2+ | blood vessels ⅓ distance to burn |
| 3+ | blood vessels ½ distance to burn |
| 4+ | blood vessels ⅔ distance to burn |
| 4.5 | blood vessels ¾ distance to burn |
| 6+ | vessels reach burn |

All evaluations were performed blindly, the investigator being unaware of which eye received tested compound and which received the vehicle. At the completion of the study, the eyes were photographed using an OM-2 camera attached to a disecting microscope.

The data from these experiments show that the burn stimulus from group to group was reasonably uniform. While the lowest concentration (0.1%) of the tested compound did not cause statistically significant decrease in mean neovascularization; the solutions with 0.25% and 0.5% concentrations of tested compound inhibited significantly neovascularization caused by silver nitrate application.

EXAMPLE 4

Endotoxin Induced Uveitis

The uvea, the middle layer of the eye, consists of the choroid, the ciliary body and the iris. Uveitis, inflammation of the uvea is characterized by change in the permeability of uvea vessels and by the leakage of inflammatory exudates into the aqueous. Uveitis may be experimentally induced by intravenous administration of endotoxin (Nature, 286:611, 1980). A model was developed in rabbits in which the uveitis, induced experimentally by endotoxin, is monitored by fluorophotometry. This experiment illustrates the utility of compounds of current invention in reducing the degree of vascular permeability developed during uveitis.

Protocol

New Zealand white rabbits were anesthetized with ketamine (35 mg/kg, i.m.) and xylazine (5 mg/kg, i.m.). dextran-isothiocyanate-fluorescein (FITC) (m.w.=64,200, 100 mg/kg as a 10% solution) was injected into their marginal ear vein. 15 minutes later, a dose of 2.5 µg/kg of endotoxin (lipopolysaccharide) isolated from Salmonella typhimurium was injected into the same marginal vein. The rabbit was placed in front of fluorophotometer and a blue light was focused into the eye. The resulting fluorescence, emitted by dextran-FITC, was detected by a photomultiplier tube. Scans were made of the right and left eyes of each rabbit after dextran-FITC administration, and 90 minutes after endotoxin administration.

The dextran-FITC concentration in the aqueous humor was determined using a fluorophotometer manufactured by Coherent Medical Division, Palo Alto, Calif. This devise consist of a scanning optic head controlled by a Commodore Pet Computer, which runs the scan, stores, and processes obtained data.

Initially, most of the dextran-FITC was present in the retinal vessels but after period of 60 minutes, considerable amount of dextran-FITC appeared in the aqueous, indicating an alteration in the vascular permeability of the vessels in the iris and ciliary body caused by endotoxin.

To test a compound, one drop of 0.5% ophthalmic solution with the tested compound as an active ingredient was applied to the right eye of the rabbit two hours prior to endotoxin injection, one hour prior to endotoxin injection, at the time of endotoxin injection, thirty minutes and sixty minutes after the endotoxin challenge. At the same times, the left eye of the rabbit received the vehicle ophthalmic solution only. The effectivity of the compound was measured by following a progressive increase in dextran-FITC leakage into the aqueous of both eyes.

The results of this study indicate that the eye pre- and post-treated with compounds of this invention were protected effectively against endotoxin-induced leakage of dextran-FITC into aqueous. Vascular permeability in treated eye was approximately ten times lower, with degree of significance smaller than 0.01 when compared with non-treated eye.

EXAMPLE 5

Effect on Increased Intraoccular Pressure

This example illustrates the effect of compounds of current invention on intraoccular pressure. Arachidonic acid, a prostaglandin substrate, when topically applied to the eye increases intraoccular pressure similarly to that observed in glaucoma.

Protocol

Female Dutch belted rabbits (Nitabell Rabbitry, Hayward, Calif.) weighing 1.5–2.0 kg were anesthetized with topical anesthetics (0.5% proparacaine HCl) obtained from Squibb. Prior to the beginning of the experiments, normal intraoccular pressure in both eyes of the rabbits were established using McKay-Marg Electronic Tonometer. Obtained results were expressed in mm of mercury. By this preliminary study it was determined that there were no significant differences in intraoccular pressure readings between the right and left eyes of normal rabbits.

The actual testing studies were divided into two substudies with the purpose for the first one to determine whether the topical application of tested compound will increase intraoccular pressure, and with the purpose of the second one to determine whether, when applied to the eye with already increased intraoccular pressure, it will be able to decrease said pressure significantly.

First Study

After the initial intraoccular pressure of each animal was determined, ophthalmic solution with 0.5% of tested compound was applied to the rabbit left eye and the vehicle ophthalmic solution was applied to the rabbit right eye. Two hours later, the pressures of both eyes were recorded, and the data were analyzed using a paired "t" test.

Neither the vehicle ophthalmic solution, nor the ophthalmic solution with 0,5% of an active ingredient increased intraoccular pressure in the two hours interval after the administration. Both measured pressures were exactly the same as those established by preliminary experiment. Thus, the tested compounds did not show any direct effect on normal intraoccular pressure.

Second Study

In the second study, the initial base-line of intraoccular pressure was again established for each animal. This was followed by application of one drop of 0.5% of the ophthalmic solution containing the tested compound as active ingredient into rabbit's left eye and the vehicle ophthalmic solution to the rabbit's right eye at the time zero and 15 minutes later. Thirty minutes from the first application of tested solutions one drop of a 2% solution of arachidonic acid dissolved in peanut oil was applied to both eyes. Forty-five minutes from the time zero intraoccular pressures of both eyes were measured and the data were analyzed using a paired "t" test.

As expected, arachidonic acid increased intraoccular pressure in the right eyes of the animals but not in the left eye which was pretreated with tested drug. Ophthalmic solution with 0.5% of the tested compound applied twice prior to arachidonic acid was able to prevent this increase in intraoccular pressure. The same solution applied only once did not significantly affect intraoccular pressure.

What is claimed:

1. A method for treating inflammation of the eye in mammals which method comprises topical application to the eye of a mammal in need thereof a therapeutically effective amount of a pharmaceutical ophthalmic composition containing 0.005-1% wt/vol of a compound chosen from those represented by the formulas:

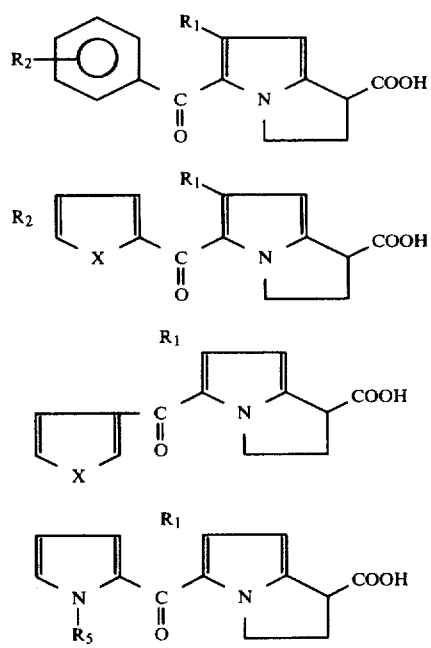

and the individual (l-) and (d-)acid isomers thereof and the pharmaceutically acceptable non-toxic esters and salts thereof, wherein $R_1$ represents hydrogen; lower alkyl group having from one to four carbon atoms; chloro or bromo;

$R_2$ represents hydrogen, a lower alkyl group having from one to four carbon atoms, a lower alkoxy group having from one to four carbon atoms, chloro, bromo, fluoro; or $R_4S(O)n$ wherein $R_4$ is lower alkyl and n is the integer 0, 1 or 2;

X represents oxygen or sulphur; and $R_5$ represents hydrogen or lower alkyl group having from one to four carbon atoms.

2. A method for treating corneal neovascularization, uveitis and cystoid macular edema in mammals which method comprises topical application to the eye of a mammal in need thereof a therapeutically effective amount of a pharmaceutical ophthalmic composition containing 0.005-1% wt/vol of a compound chosen from those represented by the formulas:

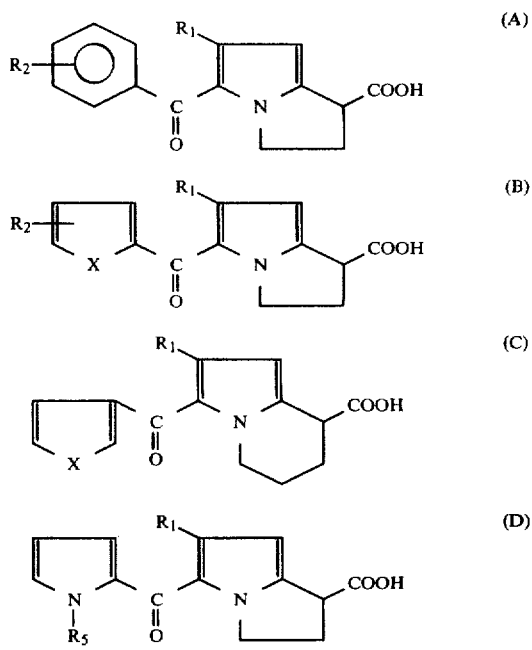

and the individual (l-) and (d)acid isomers thereof and the pharmaceutically acceptable non-toxic esters and salts thereof, wherein $R_1$ represents hydrogen; lower alkyl group having from one to four carbon atoms; chloro or bromo;

$R_2$ represents hydrogen, a lower alkyl group having from one to four carbon atoms, a lower alkoxy group having from one to four carbon atoms, chloro, bromo, fluoro; or $R_4S(O)n$ wherein $R_4$ is lower alkyl and n is the integer 0, 1 or 2;

X represents oxygen or sulphur; and $R_5$ represents hydrogen or lower alkyl group having from one to four carbon atoms.

3. The method of claim 2 for treating corneal neovascularization.

4. The method of claim 2 for treating uveitis.

5. The method of claim 2 for treating cystoid macular edema.

6. The method of claim 2 wherein compounds are represented by those of Formula (A).

7. The method of claim 6 wherein $R_1$ is hydrogen.

8. The method of claim 6 wherein $R_2$ is hydrogen, namely 5-benzoyl-1,2-dihydro-3H-pyrrolo[1,2-a]pyrrole-1-carboxylic acid.

9. The method of claim 6 wherein $R_2$ is $R_4S$ where $R_4$ is methyl and the $R_2$ substituent is at the para-position of the phenyl ring, namely 5-(p-methylthio)benzoyl-1,2-dihydro-3H-pyrrolo[1,2-a]pyrrole-1-carboxylic acid.

10. The method of claim 6 wherein $R_2$ is methoxy at the para-position, namely 5-(p-methoxy)-benzoyl-1,2-dihydro-3H-pyrrolo-[1,2-a]pyrrole-1-carboxylic acid.

11. The method of claim 6 wherein $R_1$ is methyl.

12. A topical ophthalmic pharmaceutical composition for the treatment of inflammation of the eye comprising an 99% to 99.995% wt/vol of ophthalmologically acceptable excipient in admixture with 0.005-1% wt/vol of a compound chosen from those represented by the formulas:

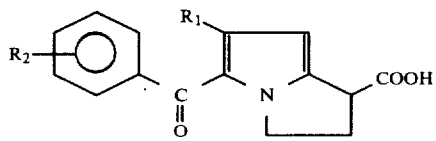
(A)

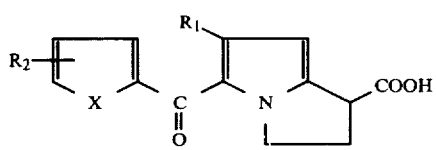
(B)

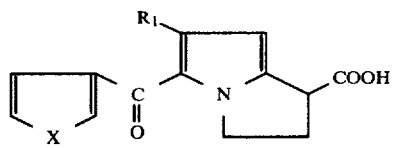
(C)

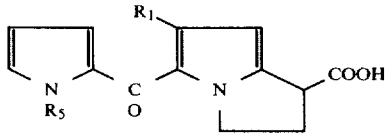
(D)

and the individual (l-) and (d-)acid isomers thereof and the pharmaceutically acceptable non-toxic esters and salts thereof, wherein $R_1$ represents hydrogen; lower alkyl group having from one to four carbon atoms; chloro or bromo;

$R_2$ represents hydrogen, a lower alkyl group having from one to four carbon atoms, a lower alkoxy group having from one to four carbon atoms, chloro, bromo, fluoro; or $R_4S(O)n$ wherein $R_4$ is lower alkyl and n is the integer 0, 1 or 2;

X represents oxygen or sulphur; and $R_5$ represents hydrogen or lower alkyl group having from one to four carbon atoms.

13. The topical pharmaceutical ophthalmic composition of claim 11 wherein the compound is represented by formula (A).

14. The topical pharmaceutical ophthalmic composition of claim 13 wherein $R_1$ is hydrogen.

15. The topical pharmaceutical ophthalmic composition of claim 14 wherein $R_2$ is hydrogen; namely, 5-benzoyl-1,2-dihydro-3H-pyrrolo[1,2-a]pyrrole-1-carboxylic acid.

16. The topical pharmaceutical ophthalmic composition of claim 14 wherein $R_2$ is $R_4S$ where $R_4$ is methyl and the $R_2$ substituent is at the para-position of the phenyl ring; namely, 5-(p-methylthio)benzoyl-1,2-dihydro-3H-pyrrolo-[1,2-a]-pyrrole-1-carboxylic acid.

17. The topical pharmaceutical ophthalmic composition of claim 14 wherein $R_4$ is methoxy at the para-position; namely, 5-(p-methoxy)-benzoyl-1,2-dihydro-3H-pyrrolo[1,2-a]pyrrole-1-carboxylic acid.

18. The topical pharmaceutical ophthalmic composition of claim 12 wherein the compound is chosen from those represented by formula (A) wherein $R_1$ is methyl.

* * * * *